(12) United States Patent
Mortimer

(10) Patent No.: US 8,156,601 B2
(45) Date of Patent: Apr. 17, 2012

(54) TOOTH CLEANING APPARATUS

(76) Inventor: John S. Mortimer, Homer Glen, IL (US)

( * ) Notice: Subject to any disclaimer, the term of this patent is extended or adjusted under 35 U.S.C. 154(b) by 156 days.

(21) Appl. No.: 11/100,176

(22) Filed: Apr. 6, 2005

(65) Prior Publication Data

US 2006/0225235 A1    Oct. 12, 2006

(51) Int. Cl.
*A46B 9/04* (2006.01)
(52) U.S. Cl. .......................... 15/167.1; 15/201
(58) Field of Classification Search .............. 15/167.1, 15/167.2, 201
See application file for complete search history.

(56) References Cited

U.S. PATENT DOCUMENTS

| | | | |
|---|---|---|---|
| 1,599,339 A * | 9/1926 | Loyd | 15/167.2 |
| 2,934,776 A * | 5/1960 | Clemens | 15/167.1 |
| 3,196,299 A * | 7/1965 | Kott | 310/81 |
| 4,224,710 A * | 9/1980 | Solow | 15/22.1 |
| 4,274,174 A * | 6/1981 | Ertel | 15/143.1 |
| 4,763,375 A * | 8/1988 | Vieten | 15/106 |
| 4,795,347 A * | 1/1989 | Maurer | 433/216 |
| 5,072,481 A * | 12/1991 | Weyer | 15/167.2 |
| 5,787,540 A * | 8/1998 | Hirschmann | 15/167.1 |
| 6,230,355 B1 * | 5/2001 | Harada | 15/167.1 |

\* cited by examiner

*Primary Examiner* — Laura C Guidotti
(74) *Attorney, Agent, or Firm* — Wood, Phillips, Katz, Clark & Mortimer

(57) ABSTRACT

A tooth cleaning apparatus having a tooth scrubbing assembly and a handle through which a cleaning portion of the tooth scrubbing assembly can be placed in operative relationship to a user's teeth and borne against surfaces of a user's teeth. The tooth scrubbing assembly is configured so that at least one of a) the cleaning portion of the tooth scrubbing assembly is preformed in a curved shape to conform to a curved arrangement of inside surfaces of a user's front teeth and b) a part of the tooth scrubbing assembly is flexible to allow conforming of the cleaning portion of the tooth scrubbing assembly to the curved arrangement of inside surfaces of a user's front teeth under a pressure as applied by a user during a tooth cleaning operation.

12 Claims, 7 Drawing Sheets

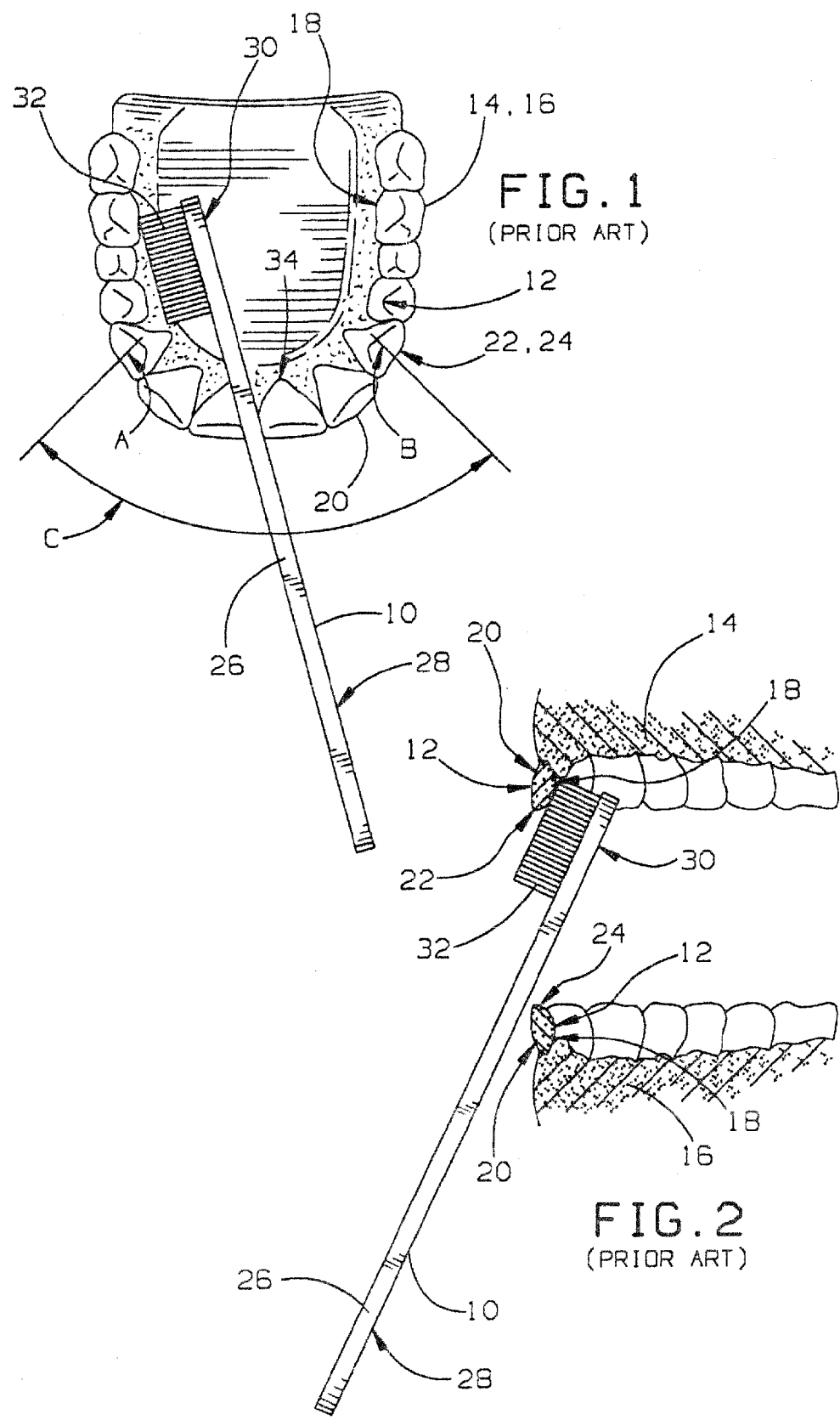

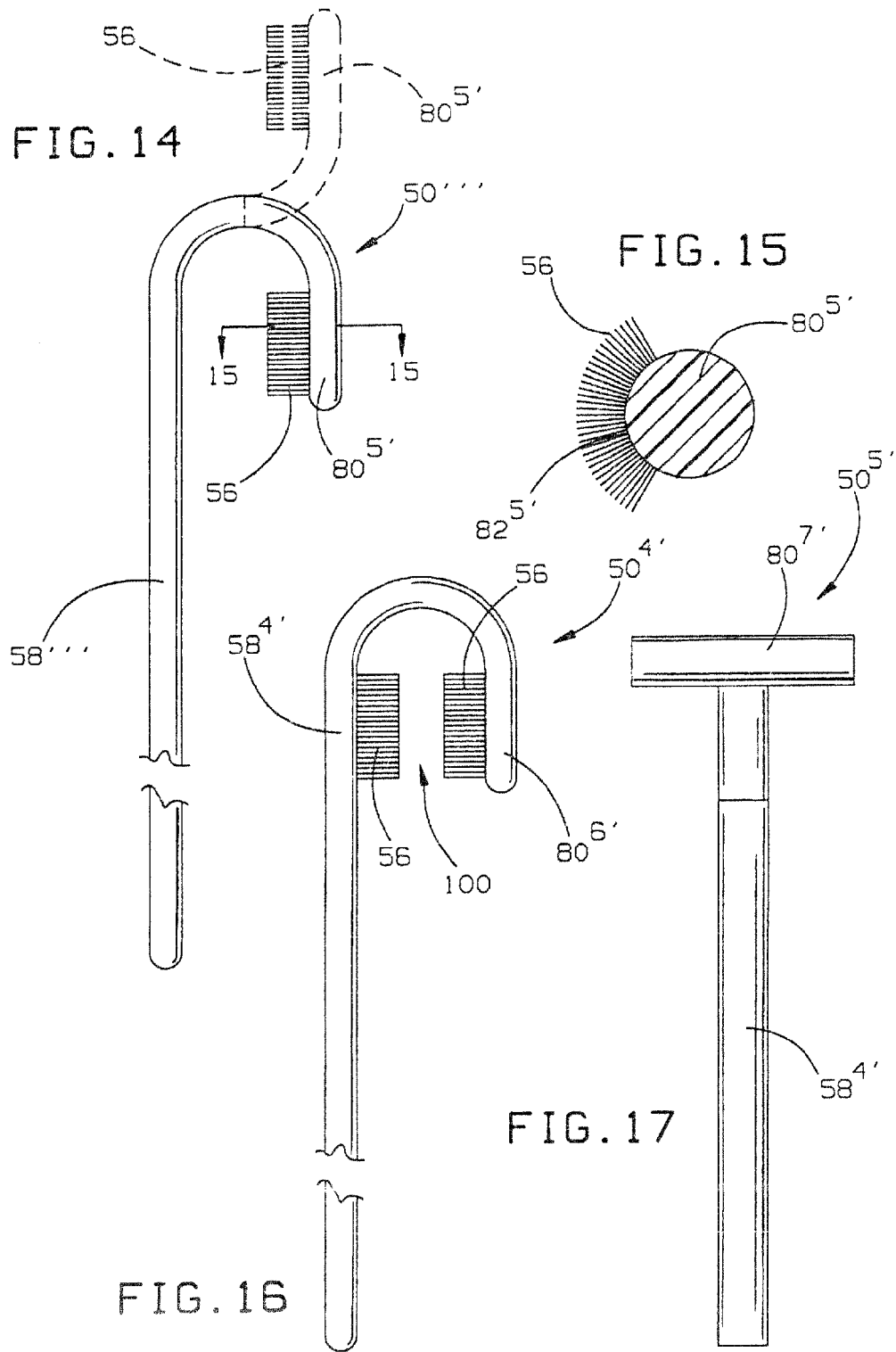

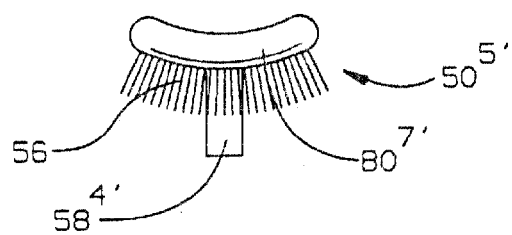
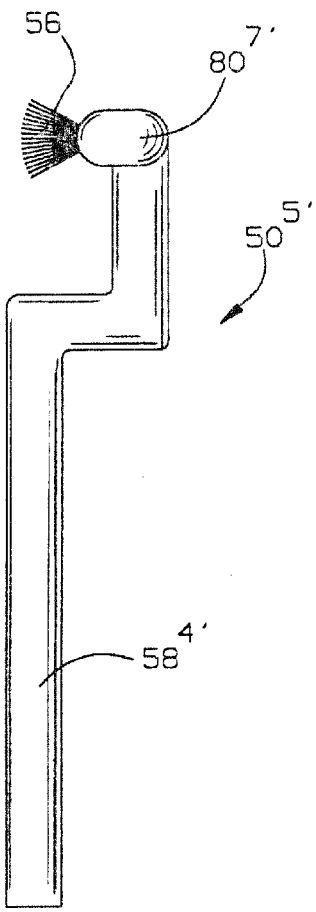
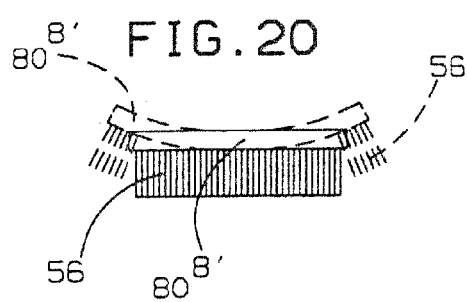
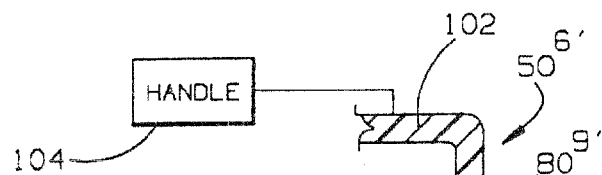
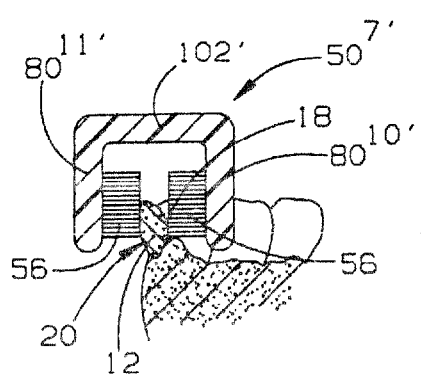
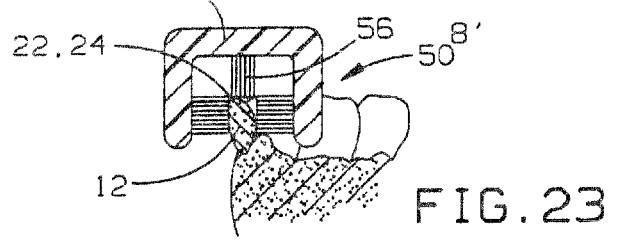

TOOTH CLEANING APPARATUS

BACKGROUND OF THE INVENTION

1. Field of the Invention

This invention relates to dental care and, more particularly, to an apparatus for cleaning teeth.

2. Background Art

Effective tooth cleaning remains an ongoing challenge to persons each day. Ideally, brushing is carried out at least once daily in a manner to thoroughly clean all exposed tooth surfaces. The tooth cleaning industry has offered a multitude of products aimed at allowing users to achieve this end.

The most basic tooth cleaning apparatus is the conventional, manual toothbrush. In its simplest configuration, this toothbrush has an elongate handle with a graspable proximal region and a distal region with flexible bristles projecting in a substantially parallel array from a generally rectangular base region. The size and shape of the "rectangle" may vary considerably.

The most common technique for cleaning teeth involves manipulating the brush to cause the bristles to move up and down during a cleaning process. This process not only effectively causes the bristles to dislodge foreign material from between the teeth and under the gums, but also stimulates the gum region. While this brushing technique can be practiced on the outside surfaces of the front teeth, it is difficult, to the point of being impractical, to practice on the back teeth and particularly on the inside surfaces of the front teeth on both the upper and lower jaws. Those conscientious about performing effective tooth cleaning generally will use the vertical brushing technique at the front jaw region, use horizontal brush strokes on the outside surfaces of teeth at the back of the upper and lower jaws, and access through horizontal strokes the inside tooth regions on the back teeth. The inside surfaces on the front teeth on the upper and lower jaws, where the jaws have a curved "U" shape, for the most part remain untreated beyond any cleaning effect resulting from being exposed to the tooth cleaning paste that migrates to thereagainst. It is so difficult to access these regions with a conventional brush that, for the most part, the inside surfaces of these teeth remain untouched by the bristles during even a relatively thorough brushing. By reason of the limited ability of persons to clean the inside front tooth surfaces on the upper and lower jaws using conventional toothbrushes, these surfaces are prone to deterioration, as through progressive plaque buildup.

Various different apparatus have been devised as an alternative to the "manual" toothbrush. It is well known to provide bristles on elements that are rotated relative to an associated handle. It is also well known to cause repetitive oscillation of bristles or vibratory movement that causes the bristles to move in a random manner. With any of these apparatus, the user need only place the bristles in contact with the tooth region to be brushed, whereupon the movement of the bristles relative to the handle effects the desired scrubbing action.

Many of these products very effectively clean the regions of teeth where the bristles are brought into contact, and have been highly commercially successful. However, they all contend with the same problem; that being that it is difficult to cause the bristles to access certain tooth regions, particularly on the inside, front regions of both jaws. While it is geometrically possible for these conventional brushes to access these hard-to-reach regions, as a practical matter, persons on a daily basis will not take the time necessary, or make the effort, to do so. Morning tooth brushing often becomes a routine that is done rather hastily. In fact, most persons brush in a fairly consistent manner that is quick and convenient, rather than thorough.

If one observes these brushing routines, it can be seen that adequate brushing occurs only at the outside tooth surfaces and potentially on the inside surfaces on the teeth on both jaws that can be readily accessed, using a toothbrush with a straight handle, at the rear region of the jaws.

As a consequence of poor brushing habits, plaque buildup on the inside tooth surfaces is inevitable, particularly at the front regions which are the most inaccessible. The teeth and the gums in this area are prone to deterioration. Many persons that brush ineffectively have had the experience of a professional tooth cleaning procedure during which the focus is on plaque removal at the inside tooth surfaces, and particularly at the front regions of the jaws.

The industry continues to seek out tooth cleaning apparatus and techniques that will allow effective cleaning of virtually all exposed surfaces of a person's teeth. In doing so, designers take into account that a daily brushing ritual is undertaken with less than total enthusiasm and with an aim towards prompt completion, rather than thoroughness.

SUMMARY OF THE INVENTION

In one form, the invention is directed to a tooth cleaning apparatus having a tooth scrubbing assembly and a handle through which a cleaning portion of the tooth scrubbing assembly can be placed in operative relationship to a user's teeth and borne against surfaces of a user's teeth. The tooth scrubbing assembly is configured so that at least one of a) the cleaning portion of the tooth scrubbing assembly is preformed in a curved shape to conform to a curved arrangement of inside surfaces of a user's front teeth and b) a part of the tooth scrubbing assembly is flexible to allow conforming of the cleaning portion of the tooth scrubbing assembly to the curved arrangement of inside surfaces of a user's front teeth under a pressure as applied by a user during a tooth cleaning operation.

In one form, the handle has a grippable portion that extends substantially in a first line around which a user's hand wraps with the user's hand gripping the grippable portion. The cleaning portion of the tooth scrubbing assembly includes at least one surface that faces generally towards the first line to engage a user's teeth during a cleaning operation.

In one form, the handle has a generally U-shaped portion which opens generally vertically with the cleaning portion of the tooth scrubbing assembly borne against inside surfaces of a user's front teeth.

In one form, the cleaning portion of the tooth scrubbing assembly includes a base on which a plurality of cleaning elements are provided and the base is one of a) preformed in a generally U shape and b) bendable into a generally U shape to conform to the curved arrangement of inside surfaces of a user's front teeth.

In one form, the cleaning elements are movable relative to the handle to produce a scrubbing action upon inside surfaces of a user's teeth.

The cleaning elements may be movable one of: a) in a rotary path; b) in a reciprocating path; and c) in a random vibratory manner.

The cleaning elements may include a plurality of flexible bristles.

In one form, the cleaning portion of the tooth scrubbing assembly is repositionable relative to the handle to selectively facilitate access to inside surfaces on teeth on a user's upper and lower jaws.

The cleaning portion of the tooth scrubbing assembly may be offset in relationship to the handle to avoid interference between the handle and one of the user's upper and lower jaws with the cleaning portion of the tooth scrubbing assembly borne against the inside surfaces of a user's front teeth on the other of the user's upper and lower jaws.

The invention is further directed to a tooth cleaning apparatus having a tooth scrubbing assembly with a cleaning portion with a first base on which there is at least one cleaning element to bear on the inside surfaces of the user's teeth with the cleaning portion in operative relationship to a user's teeth. The tooth cleaning apparatus further has a wall that extends transversely to the first base to project outwardly from the inside tooth surface and against which the at least one cleaning element bears. The at least one cleaning element faces outwardly relative to teeth against which the at least one cleaning element bears.

The at least one cleaning element may be moved on the first base in one of: a) a rotary path; b) a reciprocating path; and c) a random vibratory manner.

The tooth cleaning apparatus may further include a second base that projects transversely to the wall so that the first and second bases and wall define a substantially U shape with the tooth scrubbing assembly viewed in cross section.

In one form, there is at least a second cleaning element on one of the wall and second base that respectively bears against either of a) top or bottom surfaces of teeth and b) front surfaces of teeth with the tooth cleaning portion in operative relationship to a user's teeth and the at least one cleaning element bearing against inside surfaces of the user's teeth.

In one form, the at least one cleaning element on the first base has a plurality of bristles. The at least second cleaning element on the one of the wall and second base may also have a plurality of bristles.

In one form, there is at least a third cleaning element on the other of the wall and second base that bears against the user's teeth with the tooth cleaning portion in operative relationship to a user's teeth.

The tooth cleaning apparatus may further include a handle through which the tooth scrubbing assembly can be repositioned relative to a user's teeth.

The invention is further directed to a tooth cleaning apparatus including a tooth scrubbing assembly and a handle through which a cleaning portion of the tooth scrubbing assembly can be placed in operative relationship to a user's teeth and borne against inside surfaces of a user's front teeth. The tooth scrubbing assembly is offset in relationship to the handle to avoid interference between the handle and one of the user's upper and lower jaws with the cleaning portion of the tooth scrubbing assembly borne against the inside surface of the user's front teeth on the other of the user's upper and lower jaws.

The cleaning portion of the tooth scrubbing assembly may include a base on which a plurality of cleaning elements are provided. The plurality of cleaning elements may be movable relative to the handle to produce a scrubbing action upon inside surfaces of the user's teeth.

In one form, the tooth scrubbing assembly may be configured so that at least one of a) the cleaning portion of the tooth scrubbing assembly is preformed in a curved shape to conform to a curved arrangement of inside surfaces of a user's front teeth and b) a part of the tooth scrubbing assembly is flexible to conform the cleaning portion of the tooth scrubbing assembly to the curved arrangement of inside surfaces of a user's front teeth under a pressure as applied by a user during a tooth cleaning operation.

The cleaning portion of the tooth scrubbing assembly may be repositionable relative to the handle to facilitate access to a user's teeth at different locations.

BRIEF DESCRIPTION OF THE DRAWINGS

FIG. 1 is a plan view of a jaw on a user with a horizontally oriented, conventional toothbrush situated to brush inside surfaces on teeth on the jaw;

FIG. 2 is an elevation view of a user's jaws wherein the toothbrush in FIG. 1 is reoriented to access inside surfaces of teeth at the front of the upper jaw;

FIG. 14 is a side elevation view of another form of tooth cleaning apparatus, according to the present invention, and having a configuration generally similar to that in FIG. 13 and with a repositionable base;

FIG. 15 is an enlarged, cross-sectional view of the base taken alone line 15-15 of FIG. 14;

FIG. 16 is a view as in FIG. 14 of a further modified form of tooth cleaning apparatus with a configuration similar to that in FIG. 14, wherein the configuration is fixed and wherein additional cleaning elements are provided to allow simultaneously cleaning of opposite sides of teeth;

FIG. 17 is a rear elevation view of another modified form of tooth cleaning apparatus, according to the present invention, including a handle configured as in FIG. 3;

FIG. 18 is a side elevation view of the tooth cleaning apparatus in FIG. 17;

FIG. 19 is a plan view of the tooth cleaning apparatus in FIGS. 17 and 18;

FIG. 20 is a plan view of a further modified form of base with associated cleaning elements, according to the present invention;

FIG. 21 is a cross-sectional, partially schematic, representation of a further modified form of tooth cleaning apparatus, according to the present invention, including a base with cleaning elements and connected to a transverse wall that extends outwardly from the base;

FIG. 22 is a view as in FIG. 21 of a further modified form of tooth cleaning apparatus, with first and second bases extending transversely to a wall and having cleaning elements thereon to allow simultaneous cleaning of opposite sides of teeth;

FIG. 23 is a view as in FIG. 22 wherein cleaning elements are provided additionally on the wall to allow simultaneous cleaning of three sides of a tooth;

DETAILED DESCRIPTION OF THE DRAWINGS

Figure 3:
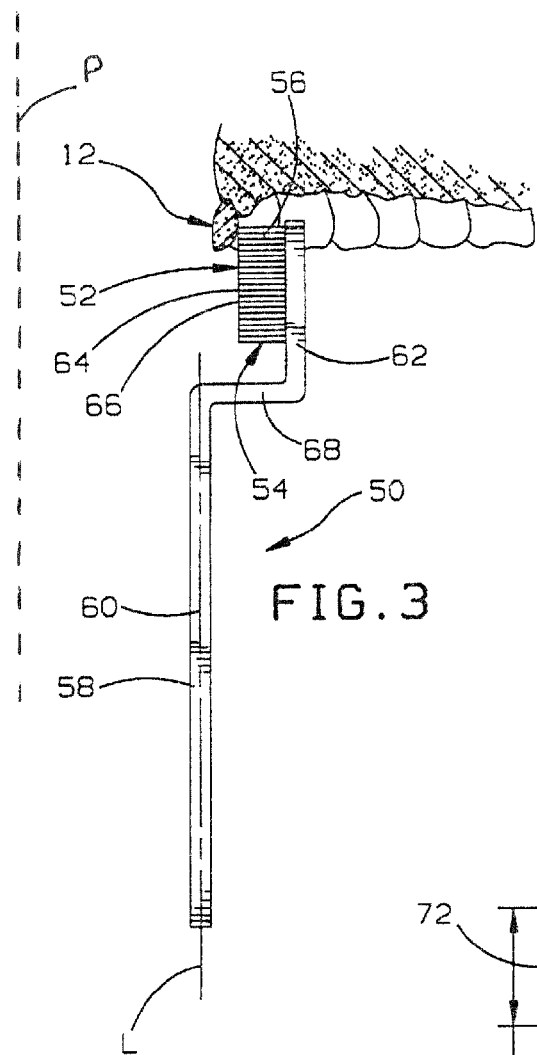
FIG. 3 is a side elevation view of one form of tooth cleaning apparatus, according to the present invention, including a handle and a base with cleaning elements thereon engaged with the inside surface of a user's teeth.

In FIGS. 1 and 2, a conventional toothbrush is shown at 10 as it is typically manipulated to clean teeth 12 on a user's upper jaw 14 and lower jaw 16. Brushing on each jaw 14, 16 involves focusing on three different areas: 1) the inside surfaces 18 of the teeth 12 on the upper and lower jaws 14, 16; 2) the outside surfaces 20 of the teeth 12 on the upper and lower jaws 14, 16; and 3) downwardly facing surfaces 22 on the teeth 12 on the upper jaw 14 and upwardly facing surfaces 24 on the teeth 12 on the lower jaw 16.

Most "manual", conventional toothbrushes have the configuration shown for that at 10 in FIGS. 1 and 2. The toothbrush 10 has an elongate handle 26 that can be gripped in any number of different manners at a proximal end 28 thereof. At the distal end 30, elongate, flexible cleaning elements/bristles 32 are mounted with a size, constitution, and spacing chosen to cause the bristles 32 to scrub the teeth surfaces 18, 20, 22, 24 as the user bears the bristles 32 thereagainst and effects movement of the bristles 32 relative to these surfaces 18, 20, 22, 24.

With the conventional toothbrush 10, the outside surfaces 20 of the teeth 22 can be readily accessed from front to rear on both jaws 14, 16. Likewise, the downwardly and upwardly facing surfaces 22, 24 can be conveniently accessed for thorough cleaning thereof using the conventional toothbrush 10.

Cleaning of the inside surfaces 18 of the curved arrangement of teeth 12 at the front region 34 of both jaws 14, 16 presents a particular challenge. With the toothbrush 10 horizontally oriented as in FIG. 1, placement of the bristles 32 against the inside surfaces 18 of the teeth 12, in the region identified by the arc A, between locations A and B, becomes difficult. First of all, the bristles 32 do not readily and uniformly conform to the U-shaped region 34 at and between the locations A, B. Additionally, there tends to be interference between the handle 26 and the user's cheeks as this maneuver is attempted. To overcome this problem, and access the full vertical extent of the teeth 12 in the front region 34, the toothbrush 10 can be reoriented generally vertically, as shown in FIG. 2. In this orientation, the horizontal cleaning dimension of the bristles 32 is substantially reduced. Further, this maneuver is sufficiently awkward and inconvenient that it is rarely undertaken.

As noted in the Background portion herein, the daily brushing routine for most is normally performed hastily. With a manual toothbrush, as shown at 10 in FIGS. 1 and 2, brush strokes are normally repeated with focus on the outside tooth surfaces 20, the downwardly and upwardly facing tooth surfaces 22, 24, and the inside tooth surfaces 18, excluding the region 34 at and between the locations A, B on both jaws 14, 16. These procedures likewise may effect less than the desired treatment of the downwardly and upwardly facing surfaces 22, 24 of the teeth in the region 34.

The industry has heretofore developed many mechanical assist mechanisms that rotate, vibrate, etc. bristles relative to a handle upon which the bristles are mounted. These toothbrushes are commonly configured generally as is the toothbrush 10 shown in FIGS. 1 and 2, with the handle having a more substantial girth to accommodate parts of the operating mechanism. However, since these toothbrushes have the same general overall configuration as the toothbrush 10, the aforementioned access problems, particularly at the region 34, are contended with.

In short, while conventional manual and mechanically assisted toothbrushes are capable of thoroughly cleaning all critical, exposed tooth surfaces, most persons are not inclined to take the time, or make the effort, to accomplish this with conventional apparatus. Brushing is commonly carried out in a manner that is convenient, as a result of which the inside surfaces of the teeth 12 at the front region 34 are often neglected, or inadequately scrubbed. As a result, the teeth in this region are prone to plaque buildup and decay.

Figure 4:
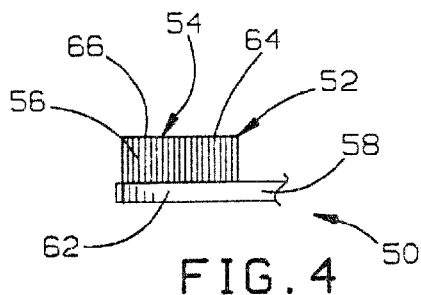
FIG. 4 is a fragmentary, side elevation view of a portion of the tooth cleaning apparatus in FIG. 3 and showing cleaning elements on a base.
Figure 5:
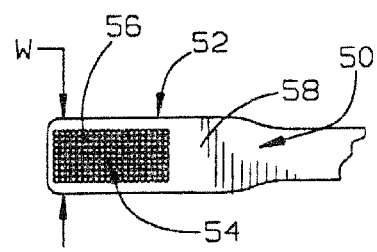
FIG. 5 is a front elevation view of the base and cleaning elements on the portion of the tooth cleaning apparatus in FIG. 4.

One form of tooth cleaning apparatus, according to the present invention, is shown in FIGS. 3-5 at 50. The tooth cleaning apparatus 50 consists of a tooth scrubbing assembly 52 having a cleaning portion 54, in this case shown as an arrangement of flexible bristles 56 that are designed to directly engage the teeth 12 during a cleaning operation. The tooth scrubbing assembly is integrated into a handle 58 through which the cleaning portion 54 of the tooth scrubbing assembly 52 can be placed in operative relationship to a user's teeth 12 and borne against the inside surfaces 18 thereof. While the tooth cleaning apparatus 50, and others described below, are particularly suitable for cleaning the inside surfaces 18 of the user's teeth 12 at the front region 34, the tooth cleaning apparatus 50, and those described below, can be used to clean the teeth 12 elsewhere. However, for purposes of simplifying the description herein, and the appended claims, the focus will be on cleaning of the inside surfaces 18 of the teeth in the region 34, with it to be understood that the cleaning apparatus 50, and others described below, can be used to clean other exposed tooth surfaces.

The cleaning portion 54 of the tooth scrubbing assembly 52 is offset in relationship to a grippable portion 60 of the handle 58, to avoid interference between the handle 58 and one of the user's upper and lower jaws 14, 16 with the cleaning portion 54 of the tooth scrubbing assembly 52 borne against the inside surfaces 18 of a user's front teeth 12 on the other of the user's upper and lower jaws 14, 16.

In this embodiment, this is accomplished by rearwardly offsetting a base 62 on the tooth cleaning apparatus 50, that carries the cleaning portion 54, from a first line L of the grippable portion 60 of the handle 58 about which a user wraps his/her hand to grip the handle 58 during use. The tooth engaging free ends of the bristles 56 define surfaces 64 that face generally towards the first line L. In this embodiment, the bristles 56 project orthogonally toward the line L. The free ends 66 of the bristles 56 are shown spaced from the line L; however, this is not a requirement.

In this embodiment, an interconnecting portion 68 of the tooth cleaning apparatus 50, in conjunction with the grippable portion 60 and base 62, defines a "Z" shape, as seen with the tooth cleaning apparatus 50 in operative relationship with the user's jaw in FIG. 3. The portion 68 can be differently configured, i.e., with a curved shape, or otherwise, to produce the offset arrangement.

As seen in FIG. 3, with the tooth cleaning apparatus 50 in this operative relationship with a user's upright head, the handle 58, base 62 and interconnecting portion 68 are configured so that: a) the cleaning portion 54 is situated within a user's mouth with the bristles 56 projecting forwardly so that the lengths of the bristles 56 extend substantially orthogonal to a vertical reference plane P (FIG. 3) in front of the user's face and parallel to the front of the user's face to conform to the inside surfaces of the user's front teeth on the user's upper jaw; b) the handle 58 is outside of the user's mouth; and c) the interconnecting portion 68 extends in a second line between the user's top and bottom laws and connects to: i) the base 62 inside the user's mouth and ii) the handle 58 outside the user's mouth. The first and second lines are at an angle to each other.

With the cleaning apparatus 50 initially in the operative relationship of FIG. 3, the user can, through movement of the gripped handle 58 in front of the user's face, move the tooth cleaning apparatus 50 vertically and horizontally relative to the user's upper jaw to thereby clean the inside surfaces on the front teeth with the cleaning surface on the user's upper jaw. As this occurs, the interconnecting portion 68 moves between the user's front teeth on the upper and lower jaws and without interference between the handle 58 and the user's upper or lower jaws.

With this arrangement, the user can conveniently direct the base 62 into his/her mouth and vertically reciprocate the handle 58 to effect the desired cleaning action. In this embodiment, as in all embodiments herein, it is contemplated that all of the cleaning portions can be either entirely manually manipulated or manipulated in conjunction with a mechanical assist mechanism.

With the structure configured as in FIGS. 3-5, one limitation is that the tooth scrubbing assembly 52 has a relatively limited horizontal width dimension, as shown at W in FIG. 5, with the length of the handle 58 generally vertically oriented. Thus, a substantial amount of horizontal shifting of the scrubbing assembly 52 may be required between the locations A and B to thoroughly cover the inside surfaces 18 of the teeth 12 in the region 34. This problem may be addressed by changing the configuration of the cleaning element/bristle pattern.

Figure 6:
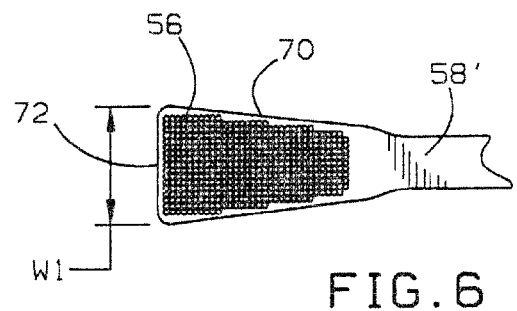
FIG. 6 is a fragmentary view as in FIG. 5 of a modified form of base on which cleaning elements are mounted.

As shown in FIG. 6, a base 70, carried on a handle 58' and from which the bristles 56 project, may have a greater areal extent. In this embodiment, the base 70 is shown as a truncated triangular shape with a free end 72 thereof having a width W1 that is substantially greater than the width W in FIG. 5.

Figure 7:
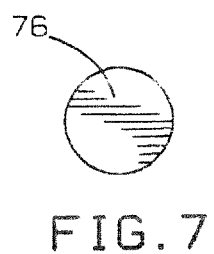
FIG. 7 is a rear elevation view of another form of base having a rounded shape.
Figure 8:
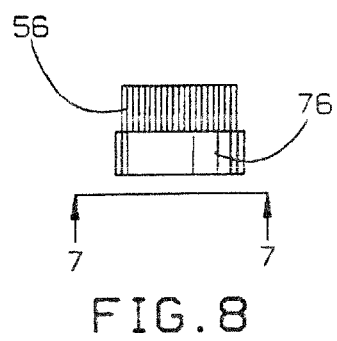
FIG. 8 is a side elevation view of the base in FIG. 7 with cleaning elements thereon.

A further exemplary configuration for a base for the bristles 56 is shown at 76 in FIGS. 7 and 8. The base 76 has a rounded shape.

In all of the embodiments shown in FIGS. 4-8, the bristles 56 project from bases having a planar surface and have approximately the same length. The lengths of the bristles 56 extend substantially orthogonally to the vertical reference plane (P in FIG. 3) in front of a user's face and parallel to the front of the user's face. The surface from which the bristles 56 project need not be planar. Further, the bristles 56 may have different lengths and constructions.

In a more preferred form, the base has a curved configuration that is particularly adaptable to cleaning the inside surface 18 of the teeth 12 at the curved front region 34. In FIGS. 9-12, curved bases 80, 80', 80", 80''' are shown.

Figure 9:
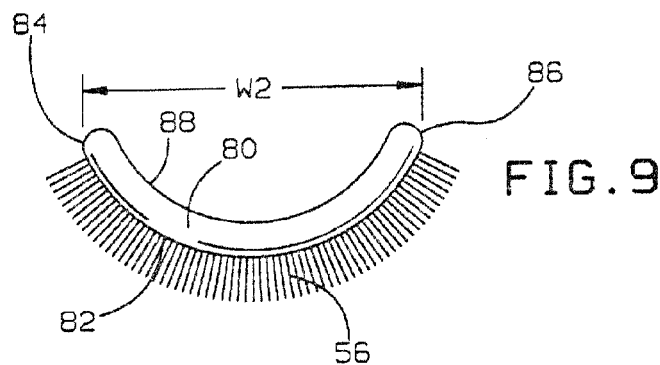
FIG. 9 is a plan view of a modified form of base with cleaning elements, according to the invention.

Referring initially to FIG. 9, the base 80 is shown with a generally U shape. It is preferred at least that the front surface 82 have a U shape with a width W2 between ends 84, 86 of the base 80. The rear surface 88 of the base 80 need not be conforming in shape, but is shown to be so in FIG. 9 to minimize the amount of material required and the resulting weight of the base 80.

Bristles 56 project from the front surface 82 substantially fully between the ends 84, 86. The bristles 56 are shown with substantially the same lengths and are of a density to produce a desired scrubbing action upon the teeth 12. The bristles 56 may be made from plastic or other materials, well known to those skilled in the art, and used on conventional toothbrushes. A first plurality of the bristles 56, such as those midway between the ends 84, 86, are aligned so that their lengths are substantially orthogonal to the aforementioned reference plane in FIG. 13. A second plurality of the bristles 56, apart from the first plurality of bristles 56, have lengths angled to the lengths of the first plurality of bristles 56. The bristles 56 in the second plurality project generally orthogonally to a plane containing the line of the length of the associated handle, as shown at L1 in FIG. 13.

In one preferred form, the shape of the base 80 conforms generally to the curved arrangement of teeth 12 at the region 34 at or between the locations A, B. The width may be wider so that teeth in substantially the entire region 34, and potentially teeth therebeyond, may be simultaneously engageable by the bristles 56 on the base 80.

Figure 10:
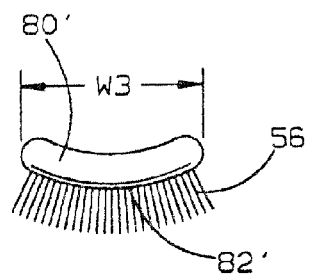
FIG. 10 is a view as in FIG. 9 of a further modified form of base wherein the base has a narrower width.

In FIG. 10, the base 80' has the same general configuration as the base 80, i.e. a curved front surface 82' with bristles 56 projecting therefrom. However, the width W3 is substantially less than the width W2. The width W2 may be on the order of 1-2 inches, but could be outside of either limit of this range.

Figure 11:
FIG. 11 is a view as in FIG. 10 wherein the cleaning elements have a different configuration.

In FIG. 11, the base 80" is shown with discrete cleaning elements 92 that are different than the bristles 56 hereinabove described. The cleaning elements 92 may be made from any material and have any shape that produces a scrubbing action against tooth surfaces when either manually moved thereagainst or moved in conjunction with mechanical assistance.

Figure 12:
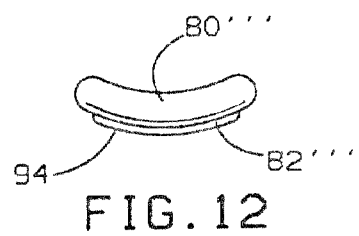
FIG. 12 is a view as in FIG. 10 wherein a cleaning element has a still further different configuration.

In FIG. 12, the front surface 82''' on a base 80''' has a cleaning layer 94 thereon that is continuous over a substantial extent. The cleaning layer 94 may be compressible and made from a material that will produce a scrubbing action. By being pressed against the teeth 12, the cleaning layer 94 conforms thereto and into the interstices, between adjacent teeth 12.

The bases 80, 80', 80", 80''' can be joined to a handle in any manner described herein, or otherwise, to facilitate location thereof at inside surfaces 18 of the teeth 12 in the region 34.

Figure 13:
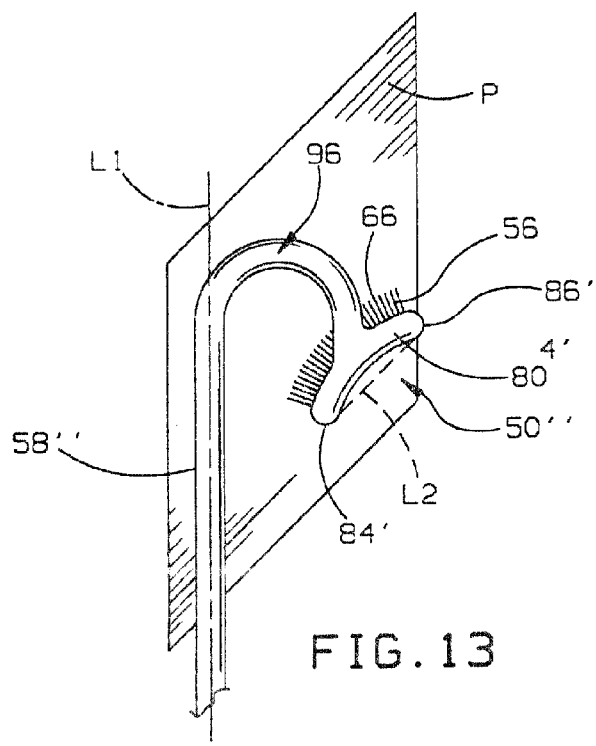
FIG. 13 is a fragmentary, perspective view of a further modified form of tooth cleaning apparatus, according to the present invention.

In one tooth cleaning apparatus, shown at 50" in FIG. 13, the handle 58" and base $80^{4x'}$, corresponding to the bases 80, 80' in FIGS. 9 and 10, are configured to define a portion with a generally vertically opening U shape at 96. The U-shaped portion 96 creates an offset between the base $80^{4x'}$ with the bristles 56 and a line L1, corresponding to the line L in FIG. 3 and representing a lengthwise extent of the handle 58" about which a user's fingers wrap in use. The cleaning surfaces/free ends 66 of the bristles 56 face generally toward the line L1. More specifically, since the base $80^{4x'}$ is curved, the free ends 66 of only some of the bristles 56 actually face the line L1. For purposes of simplicity, the language "facing the lines" L, L1, as used throughout, is intended to encompass facing a reference plane P including the line L1 and residing substantially parallel to a line L2 extending between ends 84', 86' of the base 80$^{4x'}$, assuming a symmetrical configuration thereof.

Further, in the description and claims herein, reference is made to cleaning surfaces facing in a particular direction. In actuality, the cleaning surfaces, particularly on the bases 80, 80', 80" and 80'" in FIGS. 9-12, do not have any clear, consistent directional orientation. However, for example, the bristles 56 in FIG. 9 can be considered to generally face away from the base portion from which they project, and forwardly towards the inside surfaces 18 of the teeth in the region 34 with the bristles 56 in engagement therewith.

With the arrangement in FIG. 13, the base 80$^{4x'}$ can be directed conveniently into the mouth and downwardly so that the bristles 56 thereon engage the inside surfaces 18 of the teeth 12 in the region 34. By inverting the tooth cleaning apparatus 50", the teeth 12 on the upper jaw 14 can be treated in like fashion.

In FIGS. 14 and 15, a further modified form of tooth cleaning apparatus, according to the present invention, is shown at 50'". The tooth cleaning apparatus 50'" has a base 80$^{5x'}$ that is repositionable between a solid line position and a dotted line position relative to the handle 58'". the solid line position corresponds to the configuration shown in FIG. 13. By being able to reorient the base 80$^{5x'}$ to the dotted line position, by turning around a fixed axis that is substantially orthogonal to the line of the length of the handle 58'", the apparatus 50'" can be reconfigured to a shape corresponding to that generally in FIG. 3. Thus, the inside surface 18 of the teeth 12 on both jaws 14, 16 can be conveniently accessed with an offset arrangement of the bristles 56, with the handle 58'" remaining in the FIG. 14 orientation.

In this embodiment, the base 80$^{5x'}$ has a generally cylindrical cross-sectional configuration, as seen in FIG. 15, with a curved front surface 82$^{5x'}$ from which the bristles 56 project. However, the reconfigurable design can incorporate any of the bases described herein.

In FIG. 16, a further modified form of tooth cleaning apparatus is shown at 50$^{4x'}$ and corresponds substantially to the shape shown in FIG. 14, but is not reconfigurable. Further, bristles 56 are shown on the handle 58$^{4x'}$ facing a base 80$^{6x'}$ from which bristles 56 project as in FIG. 14. With this arrangement, the teeth 12 can be placed between the bristles 56 on the handle 58$^{4x'}$ and the base 80$^{6x'}$ in the region at 100, to thereby allow simultaneous cleaning of inside and outside tooth surfaces 18, 20.

In the embodiment in FIGS. 14-16 the overall "U" shape depicted for the apparatus 50'" and 50$^{4x'}$ is actually wider than it would actually be in the usable device. This wider dimension is shown for purposes of clearly showing the structure. The width and bristle length and construction are chosen more closely based upon the normal geometry of a user's mouth and to facilitate comfortable manipulation if the apparatus 50'", 50$^{4x'}$ so as to make possible thorough tooth cleaning.

In FIGS. 17-19, a further modified form of tooth cleaning apparatus is shown at 50$^{5x'}$. The handle 58$^{4x'}$ has the same configuration as the handle 58 in FIG. 3 and supports a base 80$^{7x'}$ with bristles 56 thereon.

In FIG. 20, a further modified form of base is shown at 80$^{8x'}$. In this embodiment, the base 80$^{8x'}$ is made from a flexible material such that the base will conform to the curved tooth surfaces in response to normal pressure applied by a user during a tooth cleaning operation. That is, the base 88' may start out in the configuration shown in solid lines. When borne against a curved surface, the base 80$^{8x'}$ flexes conformingly to the dotted line position. The bristles 56 on the base 80$^{8x'}$ may have sufficient lengthwise rigidity to transmit a bending force to the base 80$^{8x'}$ while at the same time producing the described cleaning action.

Alternatively, the base 80$^{8x'}$ can be made from a material that can be bent into different shapes and will maintain those different shapes without any external force application. Thus, the base 80$^{8x'}$ can be preliminarily preformed into a curved shape and reconfigured to produce a comfortable fit that causes the bristles 56 to engage all critical surfaces during a cleaning operation. This allows custom fitting for individual user's and for different areas of the mouth.

In FIG. 21, a further modified form of tooth cleaning apparatus is shown at 50$^{6x'}$. In its simplest form, the apparatus 50$^{6x'}$ consists of a first base 80$^{9x'}$ with bristles 56 projecting therefrom in a generally forward direction. The apparatus 50$^{6x'}$ further includes a wall 102 that extends transversely to the base 80$^{9x'}$ to project outwardly from the inside tooth surfaces 18 to outside of the teeth 12, where the wall 102 directly or indirectly connects to a handle 104 through which the apparatus 50$^{6x'}$ can be manipulated.

In FIG. 22, a variation of the apparatus 50$^{6x'}$ is shown at 50$^{7x'}$, wherein a base 80$^{10x'}$ and wall 102', corresponding respectively to the base 80$^{9x'}$ and wall 102 in FIG. 21, are provided, with there further being a second base 80$^{11x'}$. The second base 80$^{11x'}$ projects transversely to the wall 102 so that the bases 80$^{10x'}$ and 80$^{11x'}$ and wall 102' on the apparatus 50$^{x'}$, as viewed in cross section, cooperatively define a U shape. The apparatus 50$^{7x'}$ can be directed over the teeth 12 at the desired location, as shown in FIG. 22. The bases 80$^{10x'}$ and 80$^{11x'}$ each have associated bristles 56 projecting towards each other to allow simultaneous cleaning of the inside and outside surfaces 18, 20 on the teeth 12.

In FIG. 23, a further variation of a structure, of the type shown in FIGS. 21 and 22, is shown at 50$^{8x'}$. The apparatus 50$^{8x'}$ has the same configuration as shown in FIG. 22, with the exception that bristles 56 are provided on a top wall 102" to allow treatment of the downwardly/upwardly facing surfaces 22, 24 of the teeth 12 on the upper and lower jaws 14, 16.

Figure 24:
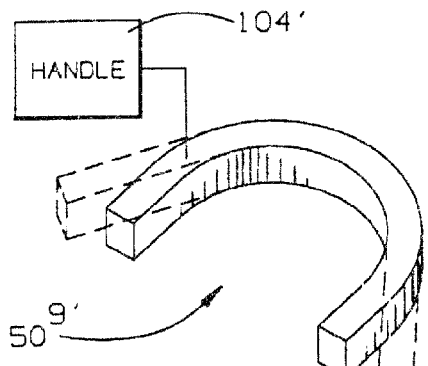
FIG. 24 is a perspective, partially schematic representation of a further modified form of tooth cleaning apparatus, according to the present invention.

The apparatuses 50$^{6'}$, 50$^{7x'}$, and 50$^{8x'}$ may be made to extend either partially or fully along the row of teeth on either jaw 14, 16. As shown in FIG. 24, the apparatus 50$^{90'}$, intended to be generic of the embodiments shown in FIGS. 21-23, as well as others, has a curved configuration to conform to and allow simultaneous treatment of all of the teeth 12 on one of the jaws 14, 16. Ideally, the apparatus 50$^{90x'}$ will have a "U" shape with a base and spaced legs. The "U" extends through at least 180° around an axis with a radius approximately the curvature of the base of the "U". A handle 104', to control movement of the apparatus 50$^{9x'}$, is optional. The material defining the portion of the apparatus 50$^{9x'}$, exclusive of the bristles 56, may have a fixed configuration, a flexible configuration, or a resettable configuration that can be selected and maintained, as shown for example by the different shape in dotted lines. The flexible configuration allows the cleaning apparatus 50$^{9x'}$ to be fit to different sizes and shapes of users' jaws 14, 16. The cleaning apparatus 50$^{9x'}$ can be releasably placed in an operative state like a conventional mouthpiece and operated manually or with mechanical assistance.

Figure 25:
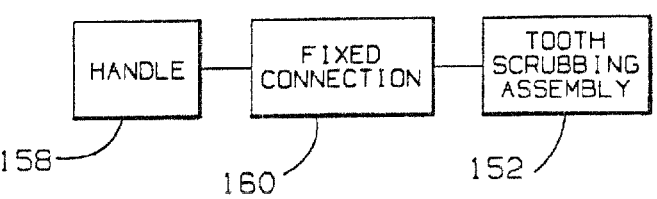
FIG. 25 is a schematic representation of a tooth cleaning apparatus, according to the present invention, with a fixed connection between a tooth scrubbing assembly and handle.
Figure 26:
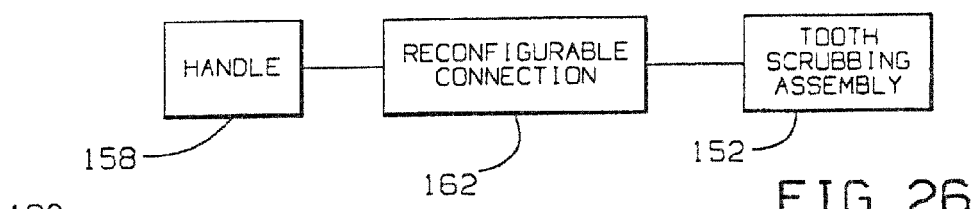
FIG. 26 is a view as in FIG. 25 wherein the apparatus is reconfigurable.

The schematic showings in FIGS. 25 and 26 are presented to encompass all contemplated variations wherein all of the components, hereinabove, and hereinbelow, described, can be mixed and matched using the broad inventive concepts described. The invention is intended to encompass any of the handle configurations, shown generically at 158, with any tooth scrubbing assembly 152. In FIG. 25, the connection between the tooth scrubbing assembly 152 and handle 158 is identified generically as a fixed connection 160.

In FIG. 26, the corresponding connection, shown generically, is reconfigurable. This is intended to encompass a pivot, floating, etc. connection, or one that can fix any number of different selected relative positions between the handle 158 and tooth scrubbing assembly 152 to facilitate a cleaning process.

Further, aside from the different configurations that can be derived using the inventive concepts and the components described above in different combinations, the invention contemplates that each and every combination might be used either in a completely manual type of apparatus, or one incorporating a mechanical assist that causes at least part of the cleaning element to be moved without any movement of the apparatus by a user. This showing is made in FIGS. 27-30. In these Figs., the cleaning element 180 is intended to represent all variations of cleaning element described herein, and otherwise, and is shown attached to a generic form of base/handle 182, such that movement between at least a part of the cleaning element 180 and associated base/handle 182 may occur.

Figure 27:
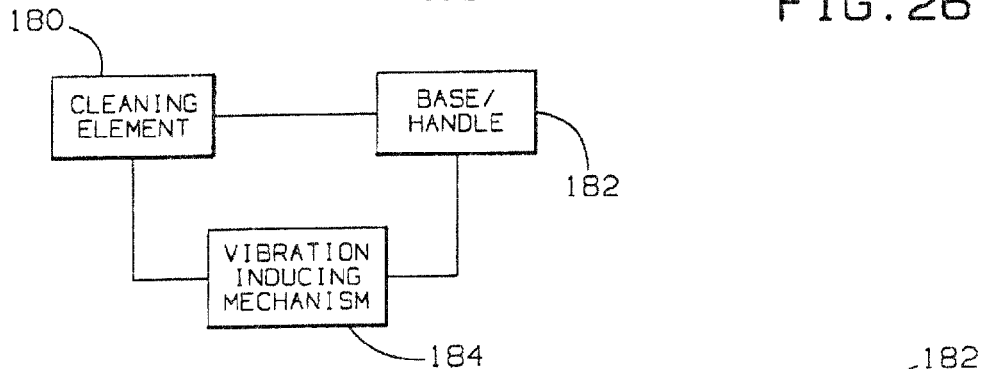
FIG. 27 is a schematic representation of a cleaning element and base/handle, including a mechanical assist mechanism for moving the cleaning element relative to the base/handle and in the form of a vibration inducing mechanism.

In FIG. 27, a vibration-inducing mechanism 184 is shown to produce random or regular vibrational movement.

Figure 28:
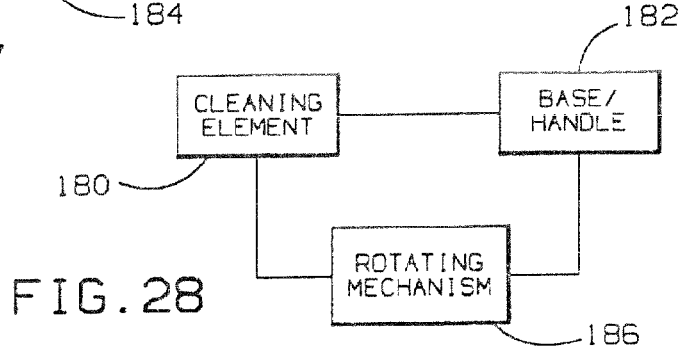
FIG. 28 is a view as in FIG. 27 wherein the mechanical assist mechanism is a rotating mechanism.

In FIG. 28, a rotating mechanism 186 is utilized.

Figure 29:
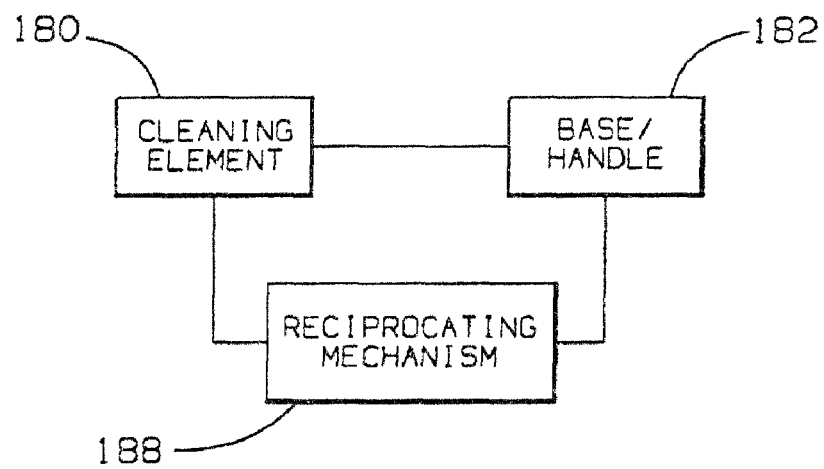
FIG. 29 is a view as in FIGS. 27 and 28 wherein the mechanical assist mechanism is in the form of a reciprocating mechanism.

In FIG. 29, a reciprocating mechanism 188 is used.

Figure 30:
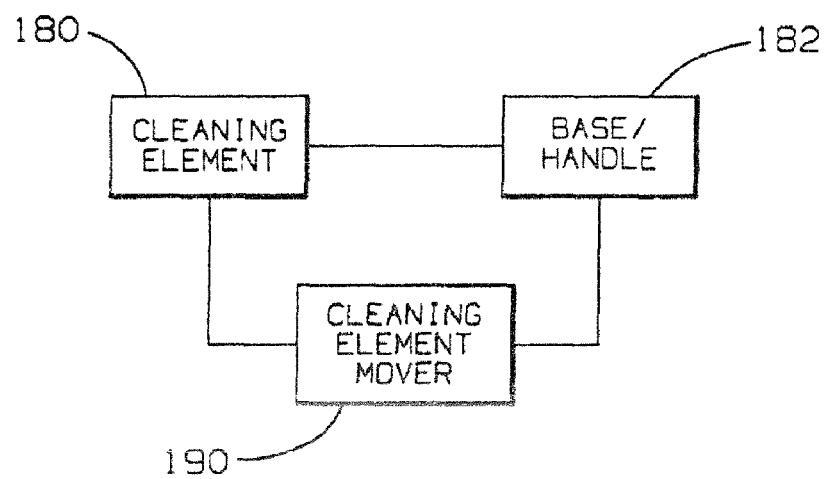
FIG. 30 is a view as in FIGS. 27-29 wherein the mechanical assist mechanism is shown more generically as a cleaning element mover.

All other types of motion are intended to be generically shown by the cleaning element mover 190 in FIG. 30.

The foregoing disclosure of specific embodiments is intended to be illustrative of the broad concepts comprehended by the invention.

The invention claimed is:

1. A tooth cleaning apparatus for cleaning teeth on upper and lower jaws of a user, the teeth on the upper and lower jaws comprising front teeth with inside surfaces, the cleaning apparatus comprising:
   a tooth scrubbing assembly comprising a cleaning portion comprising a first plurality of generally aligned bristles each having a length with a connecting end and an exposed free end spaced lengthwise from the connecting end, the exposed free ends cooperatively defining a cleaning surface;
   a handle through which the cleaning portion of the tooth scrubbing assembly can be controllably repositioned by the user,
   wherein the handle has a grippable portion with a length that extends substantially in a first line and around which a user's hand wraps with the user's hand gripping the grippable portion;
   a base to which the connecting ends of the aligned bristles are joined; and
   an interconnecting portion between the handle and the base,
   the cleaning surface fully spaced a substantial distance from, and facing generally toward, the first line to engage a user's teeth during a cleaning operation,
   the handle, base and interconnecting portion configured so that with the tooth cleaning apparatus in a first operative relationship with a user's head with the user's head upright: a) the cleaning portion is situated within a user's mouth with the first plurality of bristles projecting forwardly so that the lengths of the first plurality of bristles extend substantially orthogonally to a vertical reference plane in front of a user's face and parallel to the front of the user's face to conform to the inside surfaces of the user's front teeth on the user's upper jaw; b) the handle is outside of the user's mouth with the grippable portion spaced forwardly of the inside surfaces of the user's front teeth engaged by the first plurality of bristles; and c) the interconnecting portion extends in a second line between the user's top and bottom jaws and connects to: i) the base inside the user's mouth and ii) the handle outside the user's mouth,
the first and second lines being at an angle to each other,
   wherein the user can, through movement of the gripped handle in front of the user's face, move the tooth cleaning apparatus vertically and horizontally relative to the user's upper jaw to thereby clean the inside surfaces on the front teeth with the cleaning surface on the user's upper jaw, with the interconnecting portion thereby moving between the user's front teeth on the upper and lower jaws and without interference between the handle and the user's upper or lower jaws.

2. The tooth cleaning apparatus according to claim 1 wherein the handle, base and interconnecting portion define a generally U-shaped portion, the U-shaped portion opening in a direction generally parallel to the first line.

3. The tooth cleaning apparatus according to claim 1 wherein the base is bendable and resettable into different generally U shapes, that can be maintained without any external force application, to conform to a curved arrangement of inside surfaces of a user's front teeth.

4. The tooth cleaning apparatus according to claim 1 wherein the tooth cleaning apparatus comprises a mechanism that moves the cleaning elements relative to the handle to produce a scrubbing action upon inside surfaces of a user's teeth, with the tooth cleaning apparatus in the first operative relationship, without any movement of the apparatus by the user.

5. The tooth cleaning apparatus according to claim 1 wherein the first plurality of flexible bristles project from the base in one direction generally along a third line substantially orthogonally toward the first line and the exposed free ends of the bristles are spaced fully from the handle a distance from the first line in a direction along the third line.

6. The tooth cleaning apparatus according to claim 1 wherein the cleaning portion of the tooth scrubbing assembly is repositionable relative to the handle and maintainable in different configurations without any external force application to selectively facilitate access to inside surfaces on teeth on a user's upper and lower jaws.

7. The tooth cleaning apparatus according to claim 1 wherein the tooth scrubbing assembly is configured so that at least one of a) the cleaning portion of the tooth scrubbing assembly is preformed in a curved shape to conform to a curved arrangement of inside surfaces of a user's front teeth and b) a part of the tooth scrubbing assembly is flexible to allow conforming of the cleaning portion of the tooth scrubbing assembly to the curved arrangement of inside surfaces of a user's front teeth under a pressure as applied by a user during a tooth cleaning operation.

8. The tooth cleaning apparatus according to claim 1 wherein the cleaning portion of the tooth scrubbing assembly is preformed in a curved shape to conform to a curved arrangement of inside surfaces of a user's front teeth and the cleaning portion comprises a second plurality of bristles with lengths angled with respect to the lengths of the first plurality of bristles.

9. The tooth cleaning apparatus according to claim 8 wherein the second plurality of bristles extend substantially orthogonally to a plane containing the first line.

10. The tooth cleaning apparatus according to claim 1 wherein the base can be reoriented relative to the handle.

11. The tooth cleaning apparatus according to claim 1 wherein the base can be reoriented relative to the handle by being turned around a fixed axis.

12. The tooth cleaning apparatus according to claim 11 wherein the fixed axis is substantially orthogonal to the first line.

* * * * *